(12) United States Patent
Miura

(10) Patent No.: US 7,715,528 B2
(45) Date of Patent: May 11, 2010

(54) X-RAY DIAGNOSTIC APPARATUS

(75) Inventor: Yoshiaki Miura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/375,252

(22) PCT Filed: Jul. 27, 2007

(86) PCT No.: PCT/JP2007/064747
§ 371 (c)(1),
(2), (4) Date: Jan. 27, 2009

(87) PCT Pub. No.: WO2008/013255
PCT Pub. Date: Jan. 31, 2008

(65) Prior Publication Data
US 2010/0002828 A1    Jan. 7, 2010

(30) Foreign Application Priority Data
Jul. 28, 2006 (JP) ............................... 2006-206374

(51) Int. Cl.
*H05G 1/64* (2006.01)
(52) U.S. Cl. ...................... 378/98.12; 378/62
(58) Field of Classification Search ............... 378/62, 378/98.9, 98.11, 98.12; 600/431; 382/131
See application file for complete search history.

(56) References Cited
FOREIGN PATENT DOCUMENTS
JP    2005-027823 A    2/2005
JP    2006-034355 A    2/2006

OTHER PUBLICATIONS
International Search Report for the Application No. PCT/JP2007/064747 mailed Aug. 28, 2007.

*Primary Examiner*—Courtney Thomas
(74) *Attorney, Agent, or Firm*—Cheng Law Group, PLLC

(57) ABSTRACT

X rays are emitted without injecting an angiographic contrast material, and a non-injection image acquiring device 7 acquires a non-injection image in the angiographic contrast material non-injection state. X rays are emitted after injecting the angiographic contrast material, and an injection image acquiring device 8 acquires an injection image in the angiographic contrast material injection state. A blood vessel locus image acquiring device 9 superimposes the non-injection image and injection image acquired, and processes image data of a DSA image obtained in each of the non-injection state and injection state of the angiographic contrast material to acquire a blood vessel locus image. An image processing device 10 carries out a black-and-white reversal of the blood vessel locus image acquired, and the blood vessel is displayed in white. Beam hardening filters are inserted, and X-ray fluoroscopic radiography is carried out while inserting a guide wire W into the blood vessel. An image superposing device 11 superimposes the X-ray fluoroscopic image and the blood vessel locus image. A composite image acquired is displayed on a display monitor 15.

4 Claims, 3 Drawing Sheets

(a)

(b)

X-RAY DIAGNOSTIC APPARATUS

TECHNICAL FIELD

This invention relates to an X-ray diagnostic apparatus having an X-ray emitting device such as an X-ray tube for emitting X rays to a patient, and an X-ray detecting device such as an X-ray detector for detecting X rays transmitted through the patient and outputting X-ray detection signals, and more particularly to a technique for generating a roadmap image.

BACKGROUND ART

A fluoroscopic apparatus will be described as an example of X-ray diagnostic apparatus. The following construction is conventionally known for generating a roadmap image in this type of fluoroscopic apparatus.

As X rays are emitted from an X-ray tube to a patient, a flat panel X-ray detector outputs X-ray detection signals. Based on the X-ray detection signals, a data processor acquires X-ray images corresponding to transmitted X-ray images of the patient. The X-ray images acquired are stored in an X-ray image memory, and the X-ray images and operating menus and so on required for X-ray radiography can be displayed on a display monitor.

The data processor has a first subtraction image acquiring unit, a second subtraction image acquiring unit and a superimposition image acquiring unit. The first subtraction image acquiring unit acquires a first subtraction image as a contrast imaging subtraction image selectively showing a blood vessel filled with a contrast medium. The first subtraction image is obtained, based on the X-ray detection signals outputted from the flat panel X-ray detector in response to the X-ray emission from the X-ray tube, from an image subtraction process carried out on a radiographic image of the patient before a contrast medium injection as a mask image and a radiographic image of the patient after the contrast medium injection as a live image.

The second subtraction image acquiring unit acquires a second subtraction image without background parts (e.g. the skull) as a non-contrast imaging X-ray fluoroscopic image. The second subtraction image is obtained, based on the X-ray detection signals outputted from the flat panel X-ray detector in response to the X-ray emission from the X-ray tube, from an image subtraction process carried out on a fluoroscopic image having undergone a real-time smoothing process as a mask image and a fluoroscopic image without the real-time smoothing process as a live image.

The superimposition image acquiring unit acquires a superimposition X-ray image by superimposing, through an image addition process, the contrast imaging subtraction image acquired by the first subtraction image acquiring unit and selectively showing the blood vessel, and the non-contrast imaging X-ray fluoroscopic image acquired by the second subtraction image acquiring unit and not showing background parts (e.g. the skull).

The data processor has an image negative/positive reversing unit for carrying out, as necessary, a negative/positive reversal of the contrast imaging subtraction image acquired by the first subtraction image acquiring unit and selectively showing the blood vessel.

The above construction allows X-ray fluoroscopy with a blood vessel roadmap excluding the skull, which would obstruct confirmation of the blood vessel, to be carried out easily in real time (see Patent Document 1, for example).

[Patent Document 1]
Unexamined Patent Publication No. 2006-34355

DISCLOSURE OF THE INVENTION

Problem to be Solved by the Invention

In the conventional example, when a guide wire is inserted into the blood vessel, the guide wire can be displayed in black on a blood vessel locus displayed in white by displaying an X-ray fluoroscopic image with the guide wire inserted, as superimposed on a blood vessel locus image selectively showing the blood vessel.

However, a conventional roadmap image has a bad S/N ratio, and is hard to see, posing a problem of baffling guide wire control. This is because the fluoroscopic image showing the guide wire has a low dose.

However, increasing the dose in order to secure a good S/N ratio has a problem of being unacceptable from the viewpoint of radiation exposure reduction for the patient.

This invention has been made having regard to the state of the art noted above, and its object is to realize X-ray images with an improved depiction of a metal object such as a guide wire, without increasing the dose.

Means for Solving the Problem

To fulfill this object, this invention provides the following construction.

An X-ray diagnostic apparatus having an X-ray emitting device for emitting X-rays to a patient, and an X-ray detecting device for detecting X rays transmitted through the patient and outputting X-ray detection signals, the X-ray diagnostic apparatus comprising a non-injection image acquiring device for processing X-ray detection signals from the X-ray detecting device in a state where an angiographic contrast material is not injected, to acquire a non-injection image in an angiographic contrast material non-injection state; an injection image acquiring device for processing X-ray detection signals from the X-ray detecting device in a state where the angiographic contrast material has been injected, to acquire an injection image in an angiographic contrast material injection state; a blood vessel locus image acquiring device for acquiring a blood vessel locus image based on the non-injection image acquired by the non-injection image acquiring device and the injection image acquired by the injection image acquiring device; a radiation quality control device for controlling an energy distribution of the X rays emitted from the X-ray emitting device to the X-ray detecting device; an image superposing device for superimposing an X-ray image resulting from processing of X-ray detection signals from the X-ray detecting device based on the X rays controlled by the radiation quality control device in a state of a guide wire being inserted, on the blood vessel locus image acquired by the blood vessel locus image acquiring device; and a composite image display device for displaying a composite image superimposed by the image superposing device.

According to the construction of the X-ray diagnostic apparatus of this invention, in a state of a guide wire being inserted, the radiation quality control device controls to emit X rays in an energy band having a good ability to depict the guide wire, that is capable of depicting the guide wire in high contrast. An X-ray image excellent in the ability of depiction of the guide wire is superimposed on the blood vessel locus image acquired by the blood vessel locus image acquiring device, to obtain a roadmap image of good S/N ratio, thereby enabling control of the guide wire based on the roadmap image.

Thus, an X-ray image excellent in the depiction of the guide wire can be acquired by the control to emit X rays in an energy band having a good ability to depict the guide wire, that is capable of depicting the guide wire in high contrast. A roadmap image of good S/N ratio can thereby be obtained without increasing the dose of the X rays irradiating the patient, which enables excellent guide wire control.

In the X-ray diagnostic apparatus of this invention, the radiation quality control device is arranged to control radiation quality of the X rays emitted from the X-ray emitting device to the X-ray detecting device, to be an energy band excellent in X-ray absorption characteristic for the guide wire.

According to the construction of the X-ray diagnostic apparatus of this invention, X rays are emitted in an energy band excellent in X-ray absorption characteristic for the guide wire, to obtain an X-ray image excellent in the ability to depict the guide wire.

In the X-ray diagnostic apparatus which controls radiation quality of the X rays to be an energy band excellent in X-ray absorption characteristic for the guide wire, the radiation quality control device comprises beam hardening filters for absorbing low energy portions of the X rays emitted from the X-ray emitting device to the X-ray detecting device, thereby selecting an energy band having high X-ray absorption characteristic for the guide wire.

According to the construction of the X-ray diagnostic apparatus of this invention, low energy portions of the X rays are absorbed to emit X rays in an energy band having high X-ray absorption characteristic for the guide wire, thereby to obtain an X-ray image excellent in the ability to depict the guide wire. A roadmap image of good S/N ratio is obtained while decreasing the dose of X rays irradiating the patient M, thereby providing excellent effect in terms of radiation exposure reduction, and enabling excellent guide wire control.

In the X-ray diagnostic apparatus which controls radiation quality of the X rays to be an energy band excellent in X-ray absorption characteristic for the guide wire, the radiation quality control device is arranged to adjust a tube voltage to an X-ray tube such that the radiation quality of the X rays emitted from the X-ray emitting device to the X-ray detecting device has high X-ray absorption characteristic for the guide wire.

According to the construction of the X-ray diagnostic apparatus of this invention, by adjusting the tube voltage, X rays are emitted in an energy band excellent in X-ray absorption characteristic for the guide wire, thereby to obtain an X-ray image excellent in the ability to depict the guide wire.

Thus, since use is made of the tube voltage adjusting function possessed by the X-ray diagnostic apparatus, a new construction need not be added, to realize low cost.

EFFECTS OF THE INVENTION

According to the X-ray diagnostic apparatus of this invention, in a state of a guide wire being inserted, the radiation quality control device controls to emit X rays in an energy band having a good ability to depict the guide wire, that is capable of depicting the guide wire in high contrast. An X-ray image excellent in the ability of depiction of the guide wire is superimposed on the blood vessel locus image acquired by the blood vessel locus image acquiring device, to obtain a roadmap image of good S/N ratio, thereby enabling control of the guide wire based on the roadmap image.

Thus, an X-ray image excellent in the depiction of the guide wire can be acquired by the control to emit X rays in an energy band having a good ability to depict the guide wire, that is capable of depicting the guide wire in high contrast. A roadmap image of good S/N ratio can thereby be obtained without increasing the dose of the X rays irradiating the patient, which enables excellent guide wire control.

DESCRIPTION OF REFERENCES

2 . . . X-ray tube (X-ray emitting device)
3 . . . X-ray detector (X-ray detecting device)
4 . . . beam hardening filters (radiation quality control device)
7 . . . non-injection image acquiring device
8 . . . injection image acquiring device
9 . . . blood vessel locus image acquiring device
11 . . . image superimposing device
15 . . . display monitor (image display device)
B . . . blood vessel
H . . . patient
W . . . guide wire

BEST MODE FOR CARRYING OUT THE INVENTION

Next, an embodiment of this invention will be described in detail with reference to the drawings.

Figure 1:
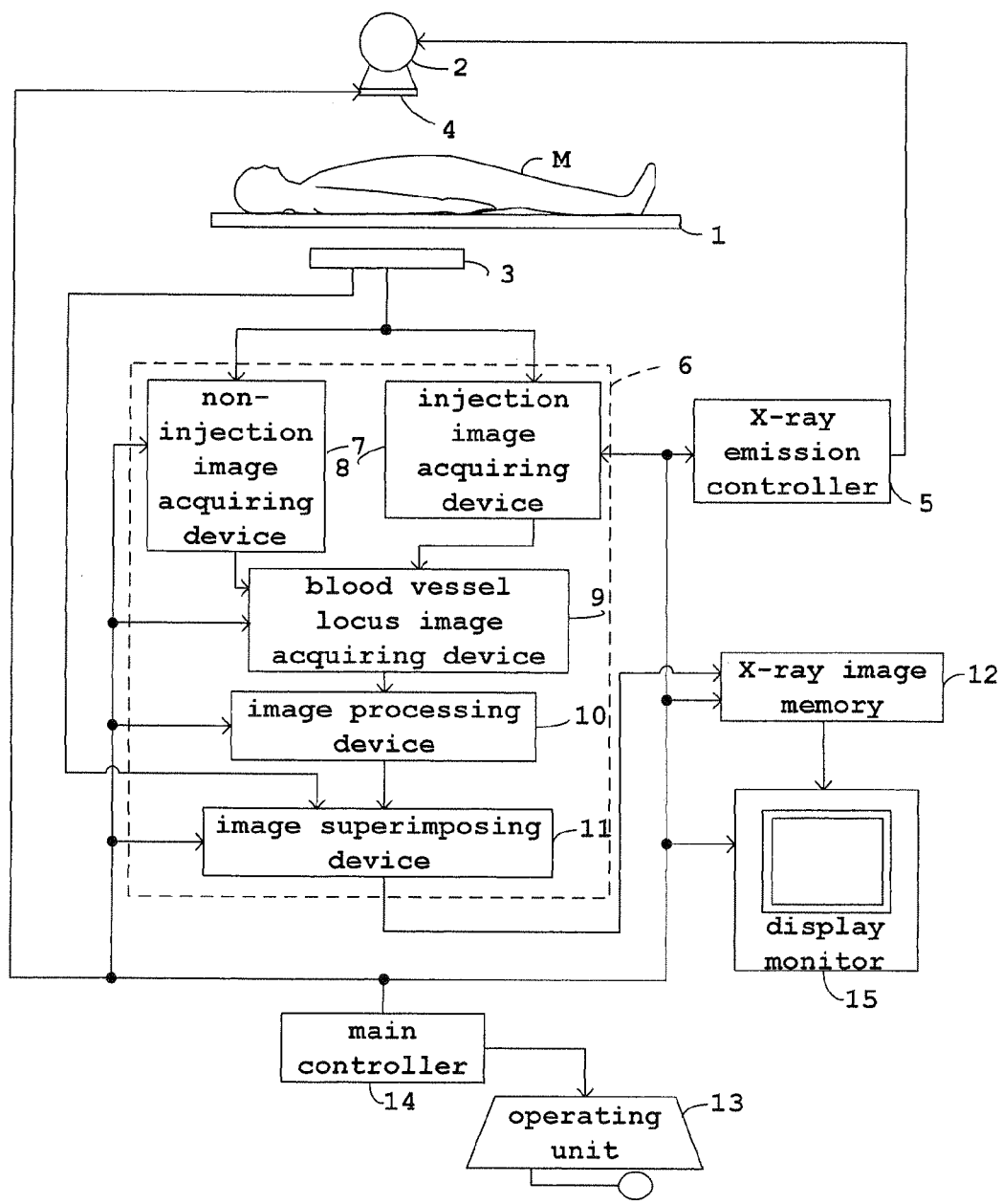
FIG. 1 is a schematic overall view showing an X-ray diagnostic apparatus in an embodiment according to the invention.

FIG. 1 is a schematic overall view showing an X-ray diagnostic apparatus in the embodiment according to the invention, which includes, as arranged across a top board 1 for supporting a patient M, an X-ray tube 2 disposed above the top board 1 to act as an X-ray emitting device for emitting X rays, and an X-ray detector 3 disposed below the top board 1 to act as an X-ray detecting device for detecting X rays emitted from the X-ray tube 2 and transmitted through the patient M. In this embodiment, an X-ray fluoroscopic apparatus will be described as an example of X-ray diagnostic apparatus.

Beam hardening filters 4 are provided on the front face in the direction of X-ray emission of the X-ray tube 2, to act as a radiation quality control device switchable between an inoperative state and an operative state for controlling an energy distribution of X rays emitted from the X-ray tube 2 to the X-ray detector 3.

Figure 3:
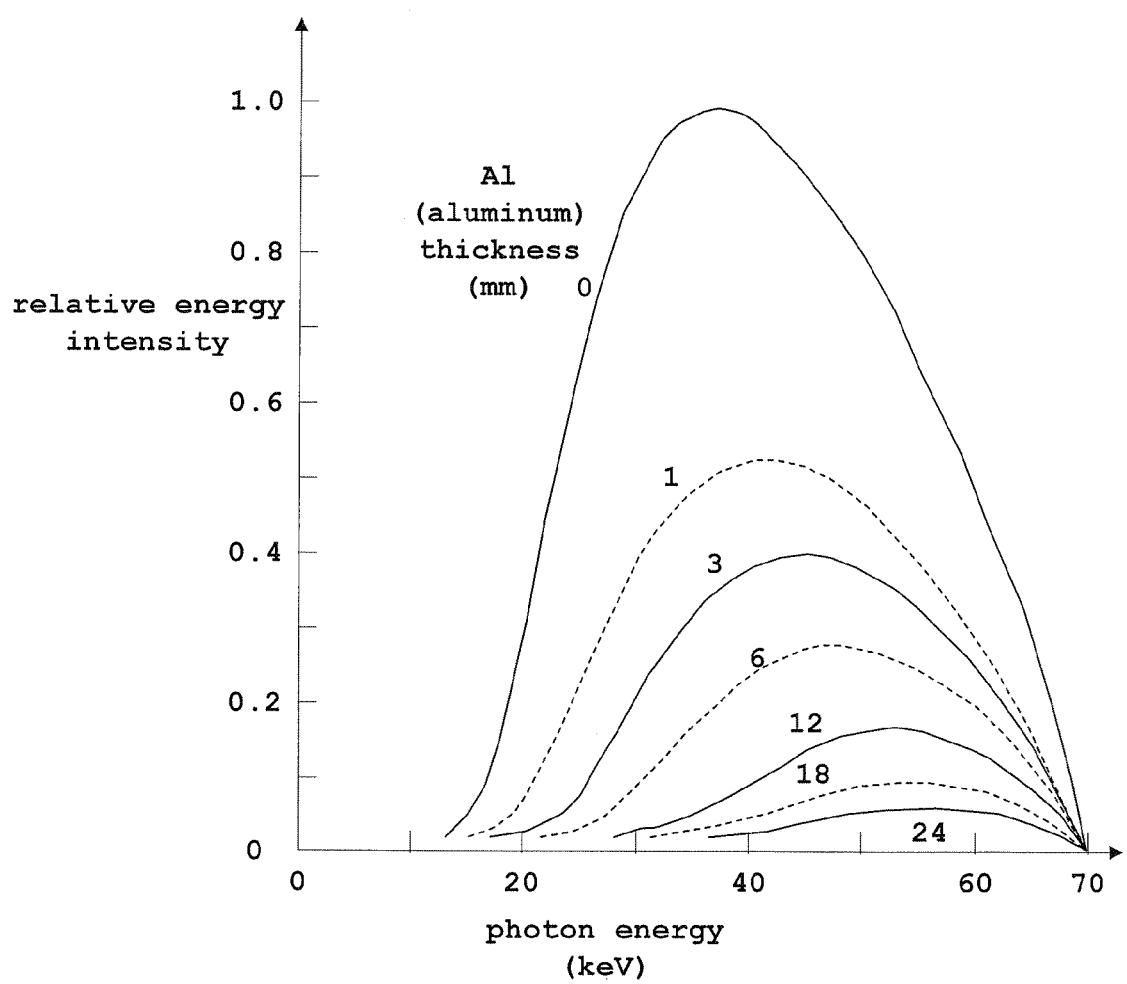
FIG. 3 shows X-ray energy distributions occurring with varied thicknesses of aluminum used as filters.

The beam hardening filters 4 are a plurality of filters constructed by combining materials different in X-ray absorption factor and shield factor, for example. The materials are combined to control a desired radiation quality according to the energy distribution of X rays as shown in FIG. 3. These materials are tantalum, copper, gold and aluminum, for example. FIG. 3 shows energy distributions of X rays occurring with varied thicknesses of aluminum as the filters. As clearly seen from FIG. 3, the quality of X rays becomes hard with high energy components.

The above "inoperative" and "operative" in this specification include not only switching all of the plurality of filters, but also switching the plurality of filters separately. Thus, what is included also is to remove only the filter which contributes most to the quality of X rays, among the beam hardening filters 4, to provide the inoperative state, and to attach only this filter to provide the operative state. It is of course possible to provide the inoperative state by removing all the filters of the beam hardening filters 4, and provide the operative state by attaching these filters.

The X-ray tube 2 has an X-ray emission controller 5 connected thereto.

The X-ray detector 3 has a data processor 6 connected thereto.

The data processor 6 includes a non-injection image acquiring device 7, an injection image acquiring device 8, a blood vessel locus image acquiring device 9, an image processing device 10 and an image superimposing device 11.

The data processor 6 has, connected thereto, an X-ray image memory 12, and a main controller 14 operable by an operating unit 13. The X-ray image memory 12 has a display monitor 15 connected thereto as an image display device. The main controller 14 has the beam hardening filters 4, X-ray emission controller 5, X-ray image memory 12 and display monitor 15 connected thereto.

The non-injection image acquiring device 7 processes X-ray detection signals from the X-ray tube 2 in a state where an angiographic contrast material is not injected, to acquire a non-injection image in the angiographic contrast material non-injection state.

The injection image acquiring device 8 processes X-ray detection signals from the X-ray tube 2 in a state where the angiographic contrast material has been injected, to acquire an injection image in the angiographic contrast material injection state.

The blood vessel locus image acquiring device 9 acquires a blood vessel locus image based on the non-injection image acquired by the non-injection image acquiring device 7 and the injection image acquired by the non-injection image acquiring device 8.

The image processing device 10 carries out a black-and-white reversal of the blood vessel locus image acquired by the blood vessel locus image acquiring device 9, to display the blood vessel in white.

Figure 2:
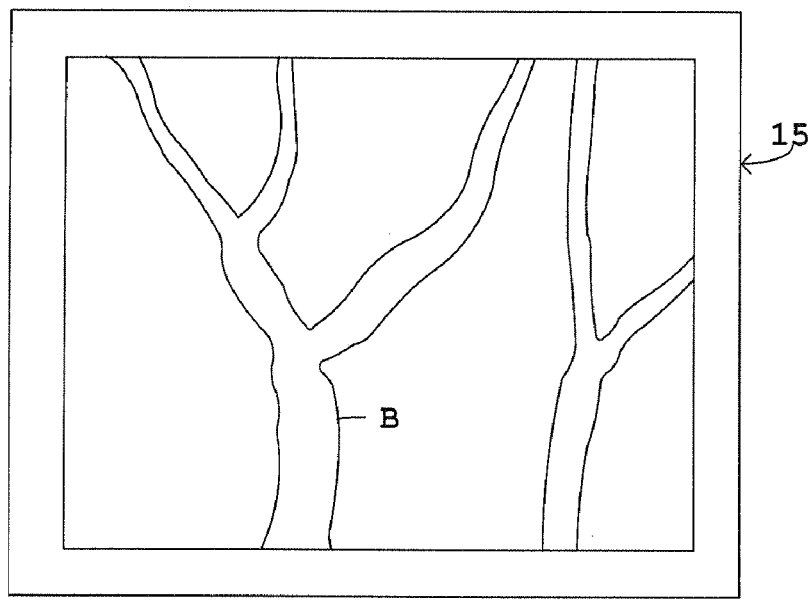
FIG. 2 shows front views of a display screen of a display monitor, in which (a) shows a state of displaying a blood vessel, and (b) shows a state of displaying a guide wire inserted into the blood vessel.
Figure 2:
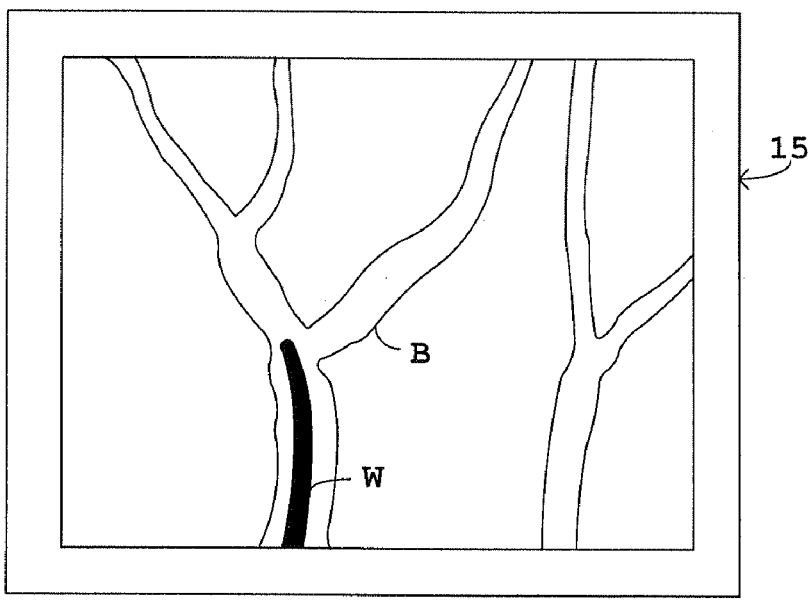

The image superimposing device 11 superimposes, on the blood vessel locus image acquired by the blood vessel locus image acquiring device 9, an X-ray fluoroscopic image obtained by processing X-ray detection signals from the X-ray detector 3 based on X rays controlled by the beam hardening filters 4 in a state of a guide wire W being inserted [see FIG. 2 (b)].

With the above construction, the beam hardening filters 4 are used to control the energy distribution of X rays emitted from the X-ray tube 2 to the X-ray detector 3. An X-ray fluoroscopy image excellent in depiction of the guide wire W is obtained without increasing the dose of X rays irradiating the patient M. This is superimposed on a blood vessel locus image, thereby to obtain a roadmap image having a good S/N ratio.

Next, a processing operation will be described.

(1) First, X rays are emitted without injecting an angiographic contrast material, and the non-injection image acquiring device 7 acquires a non-injection image in the angiographic contrast material non-injection state. Subsequently, X rays are emitted after injecting the angiographic contrast material, and the injection image acquiring device 8 acquires an injection image in the angiographic contrast material injection state.

(2) The blood vessel locus image acquiring device 9 superimposes the non-injection image acquired by the non-injection image acquiring device 7 and the injection image acquired by the non-injection image acquiring device 8 as described above, and processes image data of a DSA image obtained in each of the non-injection state and injection state of the angiographic contrast material to acquire a blood vessel locus image.

This blood vessel locus image may be acquired based on an image or radiographic image holding a peak of the X-ray fluoroscopic image obtained in each of the non-injection state and injection state of the angiographic contrast material.

(3) The image processing device 10 carries out a black-and-white reversal of the blood vessel locus image acquired as described above, and the blood vessel B is displayed in white as shown in FIG. 2 (a).

(4) The beam hardening filters 4 are switched to the operative state, and X-ray fluoroscopic radiography is carried out while inserting the guide wire W into the blood vessel B. The image superposing device 11 superimposes the X-ray fluoroscopic image and the blood vessel locus image to acquire a composite image. The composite image acquired is displayed on the display monitor 15 as shown in FIG. 2 (b). While looking at the display screen, a wiring process is carried out to control the guide wire W, and insert, thrust and round it in a predetermined site.

As the beam hardening filters 4, from experimental results of X-ray fluoroscopic radiography separately carried out beforehand, and based on the properties such as the material quality and thickness of the guide wire W used, beam hardening filters 4 are selected which are formed of a material most excellent in X-ray absorption characteristic for the guide wire W and enabling a distinct display of the guide wire W. This selection may be made by referring to the energy distributions of X ray in FIG. 3.

Where there are two or more types of guide wires W to be used, beam hardening filters 4 suitable for each guide wire W are made available. Applicable beam hardening filters 4 may be selected according to the guide wire W to be used.

Thus, with the beam hardening filters 4 selecting the radiation quality of X rays to be in an energy band excellent in X-ray absorption characteristic for the guide wire W, an X-ray fluoroscopic image excellent in the ability to depict the guide wire can be obtained. And a roadmap image of good S/N ratio is obtained while decreasing the dose of X rays irradiating the patient M, thereby providing an excellent effect in terms of radiation exposure reduction, and enabling excellent guide wire control.

The following construction also is applicable as another embodiment of this invention.

A correlation between tube voltages for emission from the X-ray tube 2 and the X-ray absorption characteristics of guide wires W to be used is determined beforehand. Based on the properties such as the material qualities and thicknesses of the guide wires W to be used, tube voltages most excellent in X-ray absorption characteristic for the guide wires W and enabling a distinct display of the guide wires W are determined. These are stored in a guide wire-tube voltage correlation table. According to a guide wire W to be used, a tube voltage corresponding thereto is selected from the guide wire-tube voltage correlation table. The X-ray emission controller 5 is controlled to provide this tube voltage.

While an embodiment has been described taking an X-ray fluoroscopic apparatus which obtains X-ray fluoroscopic images, as an example of X-ray diagnostic apparatus, this is not limitative but can be any X-ray diagnostic apparatus that acquires X-ray images such as, for example, a radiographic apparatus for acquiring X-ray images without carrying out fluoroscopic radiography.

The invention claimed is:

1. An X-ray diagnostic apparatus having an X-ray emitting device for emitting X-rays to a patient, and an X-ray detecting device for detecting X rays transmitted through the patient and outputting X-ray detection signals, the X-ray diagnostic apparatus comprising a non-injection image acquiring device for processing X-ray detection signals from the X-ray detecting device in a state where an angiographic contrast material is not injected, to acquire a non-injection image in an angiographic contrast material non-injection state; an injection image acquiring device for processing X-ray detection signals from the X-ray detecting device in a state where the angiographic contrast material has been injected, to acquire an injection image in an angiographic contrast material injection state; a blood vessel locus image acquiring device for acquiring a blood vessel locus image based on the non-injection image acquired by the non-injection image acquiring device and the injection image acquired by the injection image acquiring device; a radiation quality control device for controlling an energy distribution of the X rays emitted from the X-ray emitting device to the X-ray detecting device; an image superposing device for superimposing an X-ray image resulting from processing of X-ray detection signals from the X-ray detecting device based on the X rays controlled by the radiation quality control device in a state of a guide wire being inserted, on the blood vessel locus image acquired by the blood vessel locus image acquiring device; and a composite image display device for displaying a composite image superimposed by the image superposing device.

2. The X-ray diagnostic apparatus according to claim 1, wherein the radiation quality control device is arranged to control radiation quality of the X rays emitted from the X-ray emitting device to the X-ray detecting device, to be an energy band excellent in X-ray absorption characteristic for the guide wire.

3. The X-ray diagnostic apparatus according to claim 2, wherein the radiation quality control device comprises beam hardening filters for absorbing low energy portions of the X rays emitted from the X-ray emitting device to the X-ray detecting device, thereby selecting an energy band having high X-ray absorption characteristic for the guide wire.

4. The X-ray diagnostic apparatus according to claim 2, wherein the radiation quality control device is arranged to adjust a tube voltage to an X-ray tube such that the radiation quality of the X rays emitted from the X-ray emitting device to the X-ray detecting device has high X-ray absorption characteristic for the guide wire.

* * * * *